US011896504B2

United States Patent
Wellman et al.

(10) Patent No.: US 11,896,504 B2
(45) Date of Patent: Feb. 13, 2024

(54) PROSTHETIC WITH INTERCHANGEABLE LINER PADS

(71) Applicant: Eleos Group, LLC, Festus, MO (US)

(72) Inventors: Launius Glen Wellman, Festus, MO (US); Elizabeth Bernice Wellman, Festus, MO (US); Donald J. Fedorko, St. Louis, MO (US); Timothy Michael Stiefferman, Byrnes Mill, MO (US)

(73) Assignee: Eleos Group, LLC, Festus, MO (US)

( * ) Notice: Subject to any disclaimer, the term of this patent is extended or adjusted under 35 U.S.C. 154(b) by 0 days.

(21) Appl. No.: 18/138,813

(22) Filed: Apr. 25, 2023

(65) Prior Publication Data

US 2023/0338172 A1    Oct. 26, 2023

Related U.S. Application Data

(60) Provisional application No. 63/334,791, filed on Apr. 26, 2022.

(51) Int. Cl.
*A61F 2/80* (2006.01)
*A61F 2/78* (2006.01)
(Continued)

(52) U.S. Cl.
CPC ........ *A61F 2/80* (2013.01); *A61F 2002/5083* (2013.01); *A61F 2002/5084* (2013.01);
(Continued)

(58) Field of Classification Search
CPC .... A61F 2/60; A61F 2/601; A61F 2/76; A61F 2/78; A61F 2/80; A61F 2002/5083;
(Continued)

(56) References Cited

U.S. PATENT DOCUMENTS

| 3,074,420 A | 1/1963 | Gottman |
| 4,141,375 A | 2/1979 | Tykwinski |

(Continued)

FOREIGN PATENT DOCUMENTS

| CA | 2279026 A1 * | 2/2000 | ............. B25G 1/102 |
| WO | WO-2012022781 A1 * | 2/2012 | ............... A61F 2/60 |

(Continued)

OTHER PUBLICATIONS

Totok. Showering made easy for below-the-knee-amputees with Lytra. Amputeestore.com (Year: 2018).*

(Continued)

*Primary Examiner* — Christie Bahena
(74) *Attorney, Agent, or Firm* — CREATIVENTURE LAW, LLC; Dennis J M Donahue, III; Kevin Staed

(57) ABSTRACT

The prosthetic device is a general use prosthetic device for shower and daily mobility applications which provides a semi-custom fit. The semi-custom fitment of the leg height and anatomical sizing of the affected leg amputation are possible via configurable liner pads which can be interchanged within the support socket based on need by the wearer. The device is capable of being used on either the left or right leg with no modifications to the device and can be secured to the wearers residual limb via a friction fit between the socket liner and limb. Furthermore, an ergonomic handle and grip provides another point of control for the device to assure safety and security.

20 Claims, 8 Drawing Sheets

(51) Int. Cl.
  *A61F 2/50* (2006.01)
  *A61F 2/66* (2006.01)
(52) U.S. Cl.
  CPC ............... *A61F 2002/5089* (2013.01); *A61F 2002/6657* (2013.01); *A61F 2002/785* (2013.01)
(58) Field of Classification Search
  CPC ...... A61F 2002/5084; A61F 2002/5089; A61F 2002/6664; A61F 2002/785; A61F 3/00
  See application file for complete search history.

(56) References Cited

U.S. PATENT DOCUMENTS

| | | | |
|---|---|---|---|
| 4,459,709 A | | 7/1984 | Leal |
| 5,156,629 A | | 10/1992 | Shane et al. |
| 7,131,675 B1 | * | 11/2006 | Loucks ................ F24B 15/002 294/10 |
| 7,744,653 B2 | | 6/2010 | Rush et al. |
| 7,771,487 B2 | | 8/2010 | Mantelmacher |
| 8,778,031 B1 | | 7/2014 | Latour, Jr. et al. |
| 8,784,708 B2 | | 7/2014 | Armstrong et al. |
| 9,044,349 B2 | | 6/2015 | Hurley et al. |
| 10,548,747 B2 | | 2/2020 | Silver |
| 10,779,962 B2 | | 9/2020 | Simonette et al. |
| 10,806,607 B2 | | 10/2020 | Steinberg |
| 11,596,531 B2 | | 5/2023 | Pawlik et al. |
| 2007/0251560 A1 | | 11/2007 | Moore |
| 2016/0095723 A1 | | 4/2016 | Devito |
| 2016/0166420 A1 | * | 6/2016 | Sheehan ................ A61F 5/0118 602/7 |
| 2017/0056250 A1 | * | 3/2017 | Donovan ............. A61F 13/108 |
| 2020/0121480 A1 | * | 4/2020 | Brown ................... A61F 2/80 |
| 2021/0386565 A1 | | 12/2021 | Joseph et al. |

FOREIGN PATENT DOCUMENTS

| | | | | |
|---|---|---|---|---|
| WO | WO-2014205403 A1 | * | 12/2014 | ........... A61F 2/7812 |
| WO | 2023091732 A1 | | 5/2023 | |

OTHER PUBLICATIONS

Lytra (extrinsic evidence). Harry Teng home page. harry-teng.com/lytra (Year: 2019) 2019 via wayback machine.*
Shower Prosthetic [Online] Harry-Teng, Apr. 21, 2023. Retrieved from the Internet: <URL: www.harry-teng.com/lytra>.
Lytra Shower Prosthetic [Online] Harry-Teng, Apr. 21, 2023. Retrieved from the Internet: <URL: www.harry-teng.com/lytra-2>.
Lytra 2 Shower Prosthetic [Online] Harry-Teng, Apr. 21, 2023. Retrieved from the Internet: <URL: www.harry-teng.com/lytra-20-1>.
International Search Report, International Application No. PCT/US2023/019726, received Aug. 15, 2023, 8 pages.

* cited by examiner

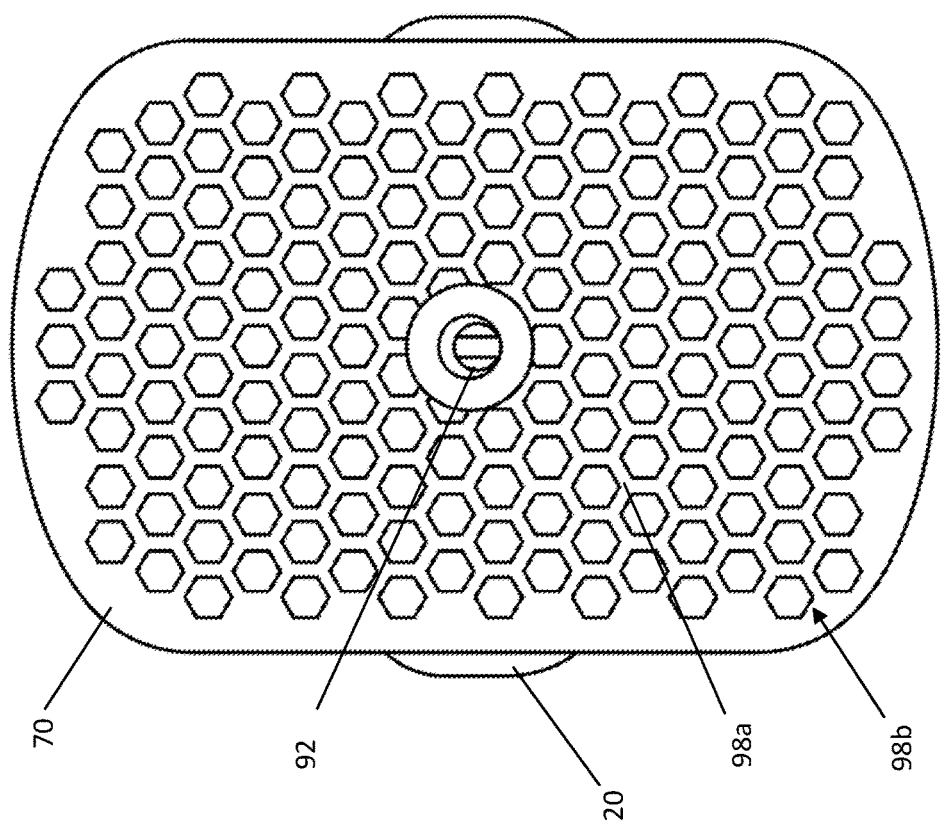
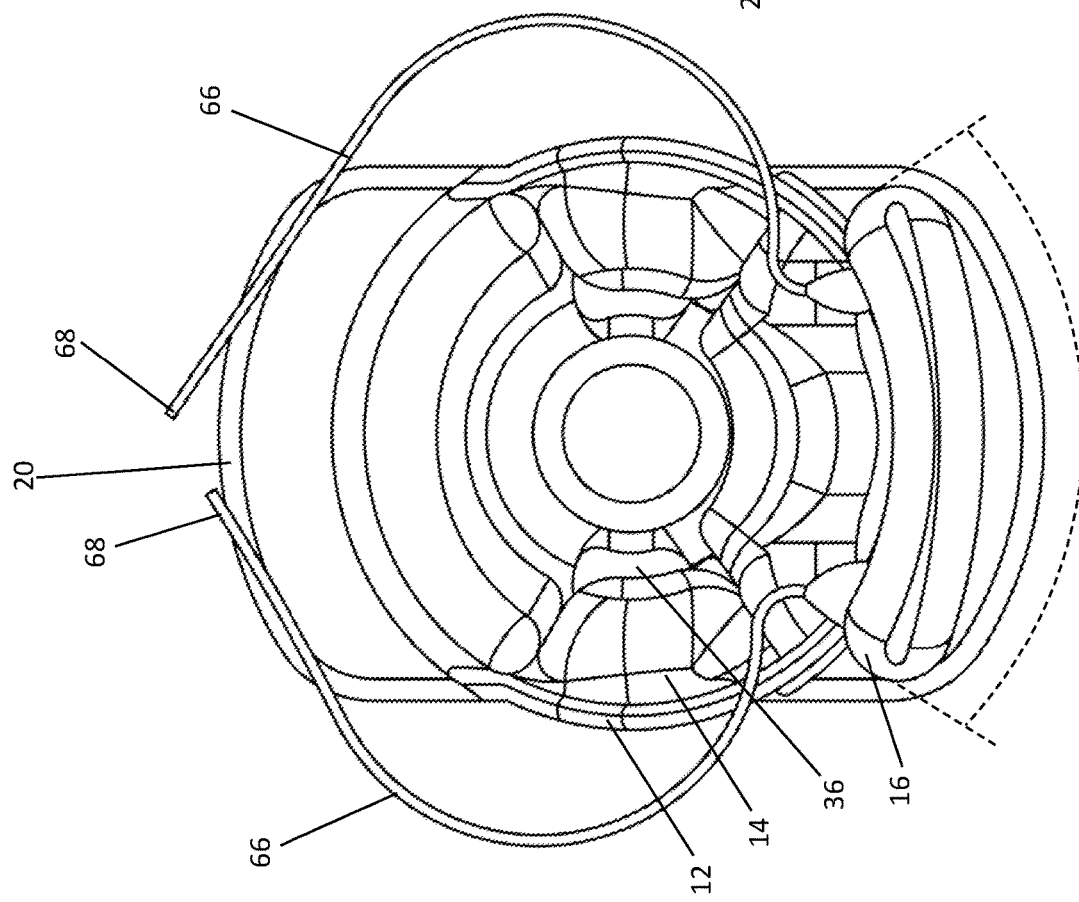

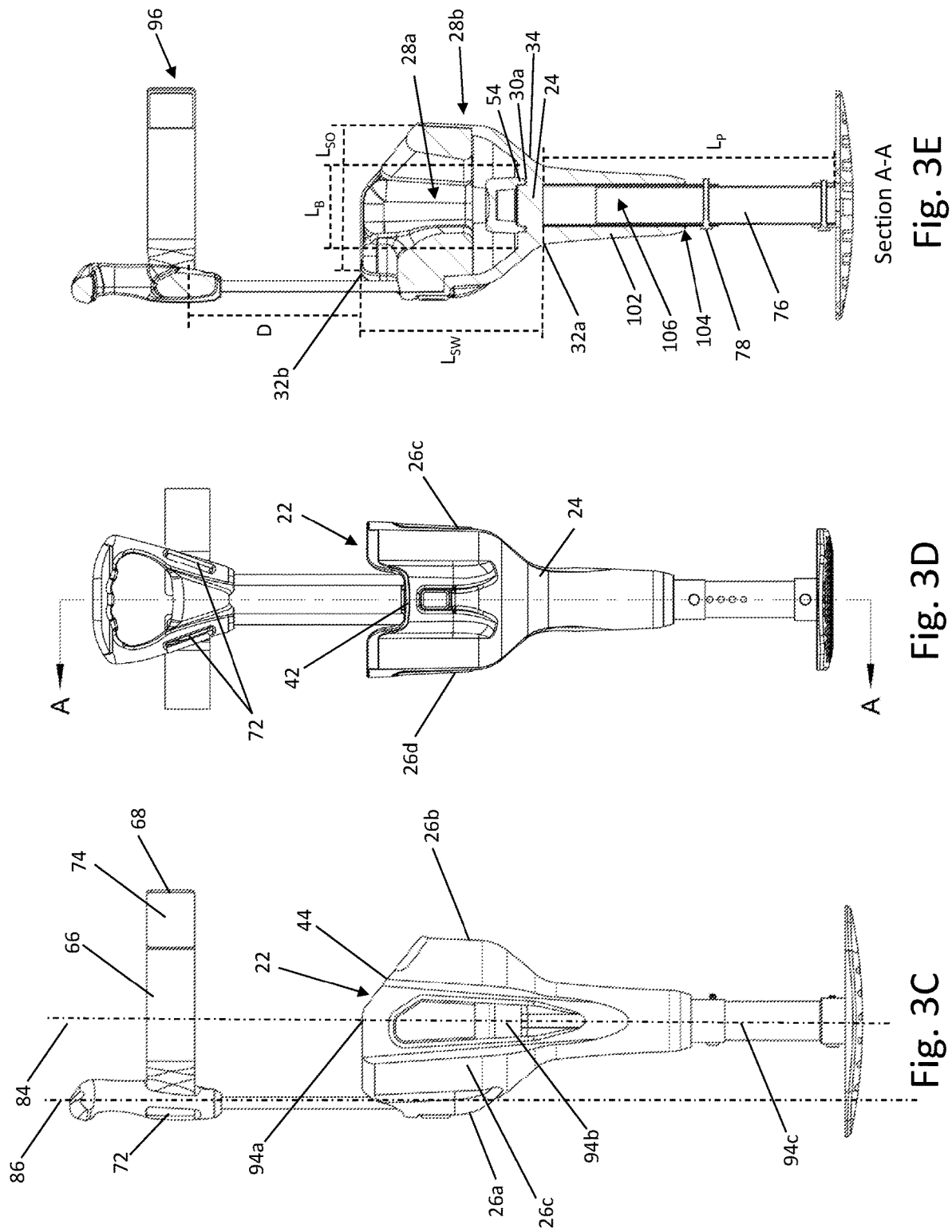

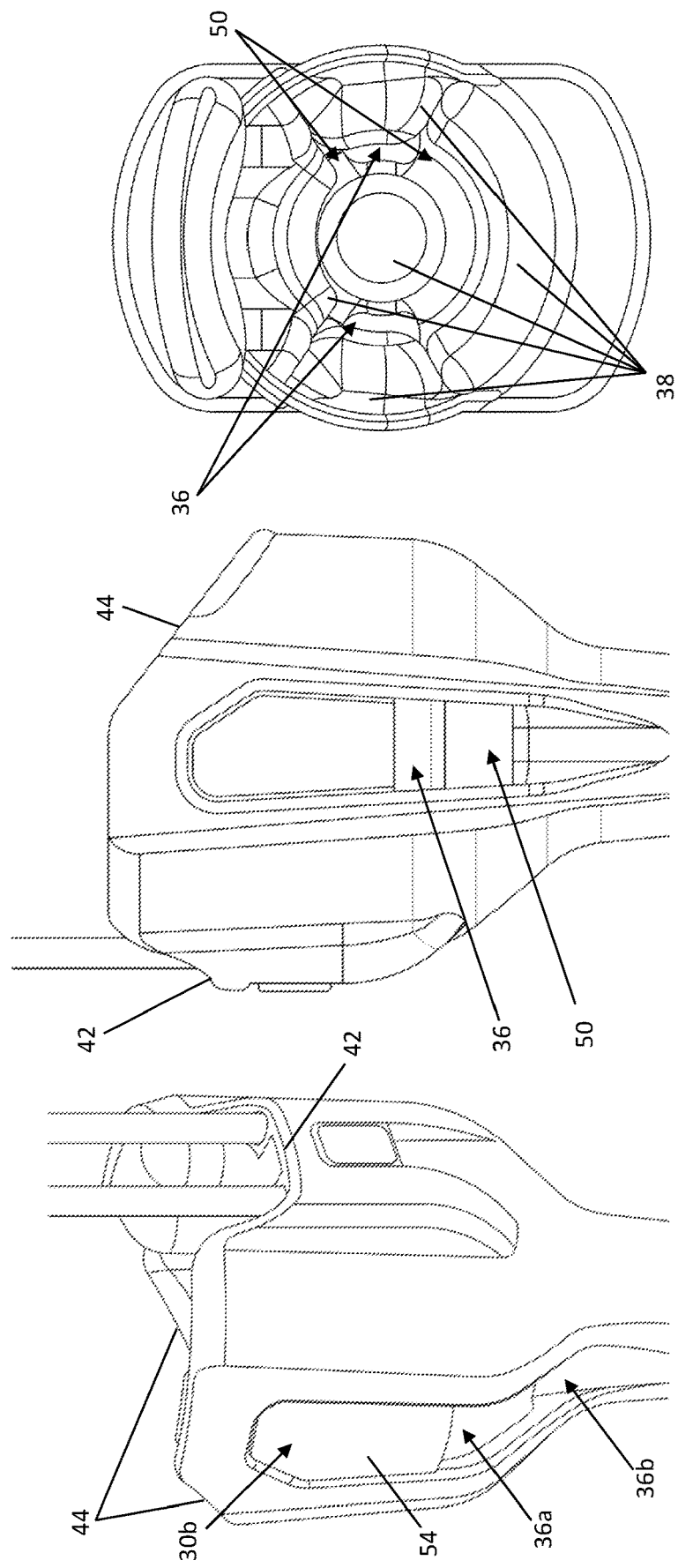

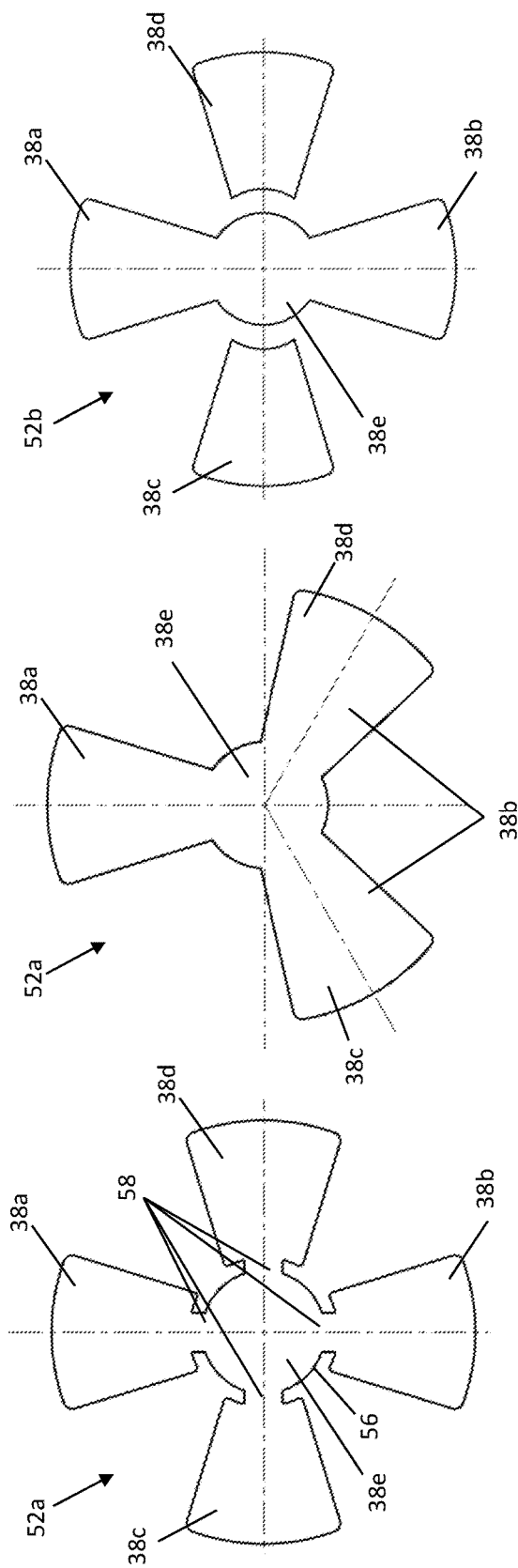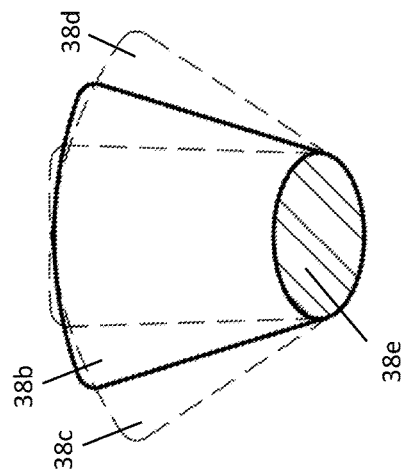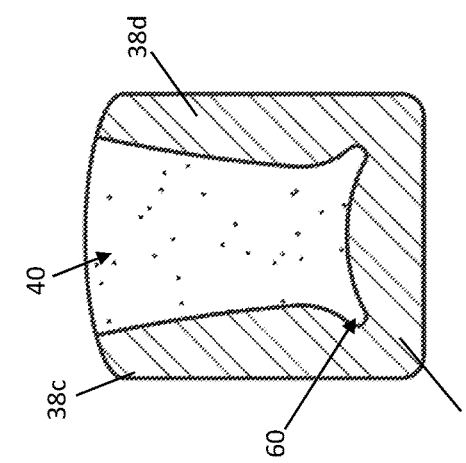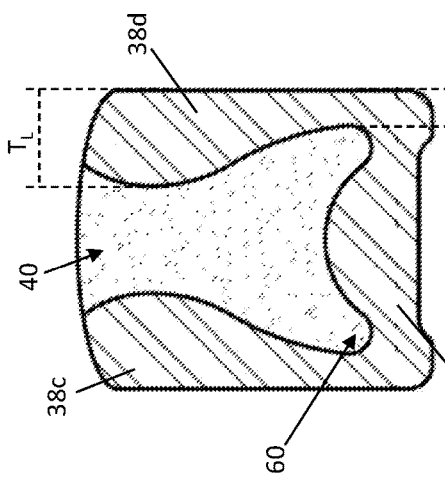

PROSTHETIC WITH INTERCHANGEABLE LINER PADS

CROSS-REFERENCE TO RELATED APPLICATIONS

This application claims priority from U.S. Provisional Patent Application No. 63/334,791 filed Apr. 26, 2022 which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to prosthetics, and more particularly to semi-custom fitment prosthetic having a modular padded lining.

Related Art

Prosthetics have been used for aiding amputees and individuals with lost arms and legs with restoration of mobility and recreational activities. These prosthetics are typically very customized and expensive devices that require a prescription and specific anatomical fitment. Furthermore, high-cost prosthetic devices are typically tailored to a specific wearer and it is generally not recommended to use these devices in wet environments. Thus, there are commonly accepted practices of covering the device with a cast protector or using a shower stool when the prosthetic is needed in a wet environment, such as when showering. Accordingly, there remains a need in the art to provide an improved prosthetic that can used by an amputee while showering without requiring a casing to reduce the risk of damaging expensive custom fit devices while also providing at least a semi-custom fitment with high mobility for the wearer.

It is advised to avoid using custom fitted prosthetics in showers, beaches and similar wet environments which could contaminate or damage the complex components of those devices. Accordingly, inexpensive, simple and universally fitting prosthetics have been developed as a supplement to custom fit prosthetics wherein an amputee can use the universal prosthetic for a limited period of time in environments that could damage their custom prosthetic. One such device is the LYTRA™ prosthetic line which has multiple alternative designs, including those shown in FIGS. 1A and 1B. Although simple to make and use, the LYTRA™ devices are one-size-fit all and do not provide any custom-fit to the wearer beyond simply adjustment of the strap used to secure the residual limb to the prosthetic. Thus, the wearer has limited means to adjust the device to improve comfort or function.

Other devices include U.S. Pat. Nos. 10,548,747 and 4,459,709 which are directed to socket-type temporary prosthetic leg devices which are suitable for showering. To provide added comfort and a more custom-fit, the '747 Patent describes the use of multiple inflatable bladders within the basket that holds the residual limb. Although the inflatable bladders allow the wearer to adjust the device to improve comfort, the device is inherently limited because the inflatable bladders are not modular and cannot be interchanged by the wearer. Inflatable bladders are also limiting because they require the wearer to manually inflate the bladder to the desired pounds for square inch (PSI), which generally requires some trial and error as they adjust the fit. Furthermore, the device neither includes an ergonomic handle that a wearer can grasp for added control and functionality nor provides the option for a secondary strap to create a more secure attachment between the device and the residual limb.

The '709 Patent describes a socket-type prosthetic that is fit to the wearer at the outset and molded into a specific size. This device therefore includes many of the issues inherent to prosthetics in that it requires an initial sizing step before the device can be made and worn. Once made, the device does not provide any further customization or adjustment means that allow the wearer to increase the comfort and functionality.

Accordingly, there remains a need for an improved prosthetic that allows for a fully custom fit with a socket liner that does not require a fastening strap and which can be used in a shower without the risk of collecting water.

SUMMARY OF THE INVENTION

The prosthetic device described herein is a general use prosthetic device for shower and daily mobility applications. While the inception of the device was rooted in a cost effective, shower specific prosthetic, it provides as a semi-custom fit prosthetic for those without access to higher end devices or for those who wish to only use their fully custom fit devices in friendly environments. The device aims to reduce the time required preparing for showering as well as providing a safe and effective way of entering and exiting the shower. In addition, it will provide a rapid attachment method that allows it to be a quick and viable prosthetic for around-the-house use.

The device is intended to be available to the wearer as a semi-custom fit, at a low cost and allow the wearer to choose the appropriate size pads to achieve the proper fit. The device is also specifically designed to be used in locations that a typical custom prosthetic use would not be recommended.

As described herein, various embodiments of the invention comprise devices and methods for attaching and securing the device to allow mobility and return to function and activities. The securing device allows for the prosthetic to be conveniently attached and secured by a single person so that no assistance is required. Semi-custom fitment of the leg height and anatomical sizing of the affected leg amputation are possible via configurable pads. The device is capable of being used on either the left or right leg with no modifications to the device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 3A, 3B, 3C, 3D and 3E respectively show top, bottom, side, front and cross-sectional views of the embodiment of the prosthetic device shown in FIGS. 2A and 2B.

FIGS. 4A, 4B and 4C respectively show a perspective view, a side view and a top view of the socket and drain port according to the preferred embodiment of the invention described herein.

FIGS. 6A, 6B and 6C each show top plan views of alternative embodiments of the liner according to the invention described herein.

FIGS. 7A-7C respectively show cross-sectional side views of the alternative embodiments of the liner shown in FIGS. 6A, 6B and 6C.

DETAILED DESCRIPTION OF THE PREFERRED EMBODIMENTS

Figure 1B:
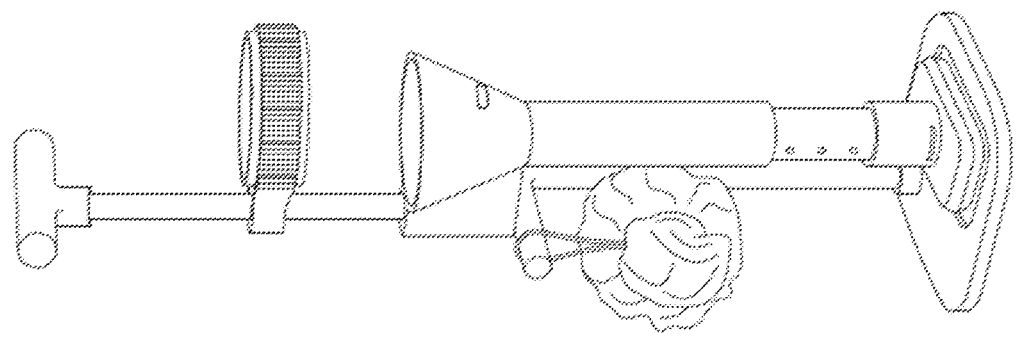
FIGS. 1A and 1B show prosthetic devices in the prior art.
Figure 1A:
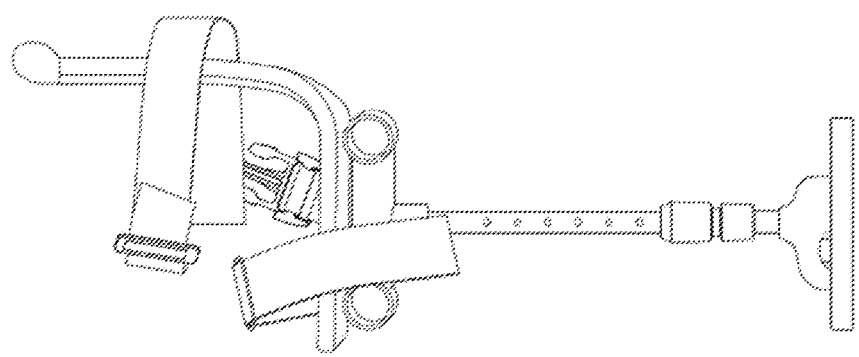

The following description of the preferred embodiment(s) is merely exemplary in nature and is in no way intended to limit the invention, its application, or uses.

The prosthetic 10 according to the invention described herein is device designed for a wearer 100 having a residual limb 105, such as an above the knee or below the knee amputee. The prosthetic includes a socket having a padded liner, footplate connected to the socket by a pylon and a handle. In the preferred use, the wearer can rapidly insert a residual limb into the socket after preparing for a shower and thereby walk to and from the shower without any other aides. Given the intended use is in a shower, or similarly wet environments, the device according to the preferred embodiment is made from materials which withstand wet environments. The fit of the socket can be customized to the particular wearer by swapping out the interchangeable modular liner pads based on a desired thickness of configuration. The height of the prosthetic can be adjusted with a telescoping pylon with separate sections that telescope between a fully extended and a fully retracted position. In addition, a handle extends from the superior end of the socket and can be grasped by the wearer to provide another point of control for the prosthetic.

Although persons having an ordinary skill in the art will appreciate that the prosthetic device described herein could be made from many types of materials without departing from the innovative aspects, the preferred embodiment of the device is constructed from non-porous and corrosion resistant materials. Furthermore, the innovative construction and drain features integrated into the device significantly decrease, if not eliminate, the chances of water entrapment between the various components. The main socket of the device and handle are preferably constructed from a rigid polyurethane foam with high strength and a solid wall design to eliminate the concern of bacteria and mildew growing from water entrapped. The adjustable pylon and footplate are designed using corrosion resistant aluminum and stainless-steel components. As further detailed below, the footplate also includes a rubber foot pad formulated from soft durometer rubber to assure non-slip footing in wet environments. All hardware and coupling components of the footplate are also fabricated from corrosion resistant and lightweight materials. The removable liner pads situated within the socket are preferably made from a reaction injection molded (RIM) soft durometer foam but may be also be pneumatic pads which are not only a non-absorbent surface that is suitable for wet environments but also allow for customizable and conforming fitment of the device to the wearer.

The socket 12 has a basket shape with an opening 22 and interior volume 28a that receives the residual limb, a base 24 opposite from the opening and a sidewall 26 extending a length ($L_{SW}$) from their inferior end 32a connected to the perimeter 34 of the base to their superior end 32b which surround the opening and are radially offset from a center vertical axis. Preferably, the socket is a single-size basket for all adult prosthetics that provides for economies of scale in producing the device with the modular liner described below being available in a variety of configurations and thicknesses to address individual wearer needs. However, it will be appreciated that the socket could be a range of sizes and the relative dimensions of the sidewall, base and openings are not intended to be limiting. For example, to accommodate a wearer with a wider residual limb, such as for an above the knee amputee who will insert their thigh into the socket, the cross-sectional length ($L_{SO}$) of the socket opening may be larger than the sidewall length whereas another embodiment may have sidewalls that are equal to or greater than the diameter of the socket opening, such as for a below the knee amputee who's calf is inserted into the socket. Further still, the relative dimensions of the base are also not intended to be limiting such that the cross-sectional length ($L_B$) of the base may be less than the cross-sectional length of the socket opening in one embodiment but equal to the diameter of the socket opening in another embodiment.

As particularly shown in FIGS. 3C, 3D and 3E, the sidewall of the socket includes an anterior section 26a, a posterior section 26b, a medial section 26c and a lateral section 26d which collectively define the preferred cylindrical shape. Each sidewall section is substantially vertical and the base is substantially horizontal with the respective inferior ends of each section fixedly connecting to the perimeter of the base to form a unitary socket.

The superior end of the socket sidewall also has an ergonomic geometry to provide an increased range of motion to the wearer. More particularly, the anterior section of the sidewall preferably includes an inferiorly recessed segment 42 relative to the superior end of at least one of the lateral and medial section of the socket. As explained below, the post of the handle preferably connects to this recessed segment and the recess provides clearance for the kneecap of wearer who has a below the knee amputation. By adjusting the position of the residual limb within the socket via the kit of selectable pads discussed below, the wearer can secure their residual limb within the socket but also position their knee cap at a location that is aligned with recess. Thus, during normal gate, knee flexion will not be inhibited by the anterior section of the socket sidewall. To provide further range of motion, it is also preferred that the posterior section of the sidewall have a slope 44 that is inferiorly downward from one of the lateral and medial sections. Similar to the recessed segment in the anterior section that provides clearance for the knee cap of the wearer, the slope in the posterior section provides clearance for the posterior portion of the wearer's thigh during normal gate.

The base of the socket in the preferred embodiment also includes a longitudinal protrusion 102. As illustrated in FIG. 3E, the longitudinal protrusion extends downward from the perimeter of the base in the opposite direction of the sidewalls and has an open bottom 104 with an internal bore 106 that receives the proximal end of the pylon. However, it will be understood that alternative embodiments may not include the longitudinal protrusion on the exterior 28b of the socket and instead connect to the socket pylon by alternate means.

Figure 2B:
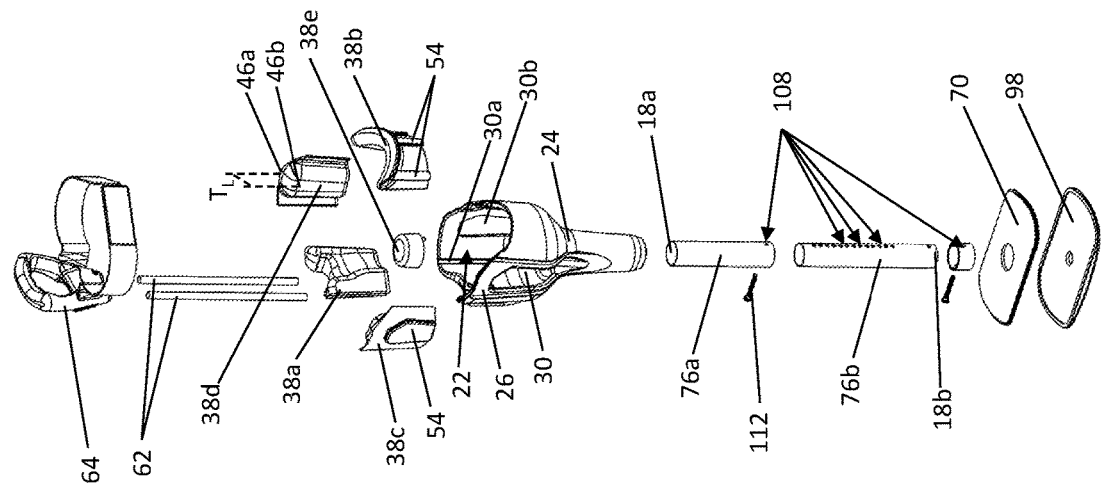
FIGS. 2A and 2B are respectively a perspective view and an exploded view of an embodiment of the prosthetic device according to the invention described herein.
Figure 2A:
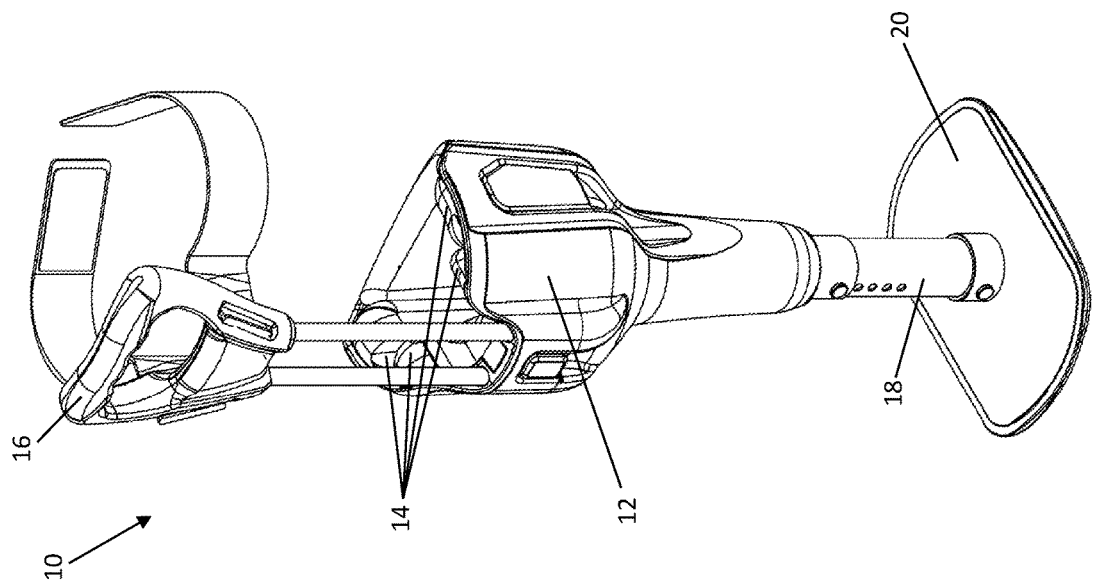

Similar to the relative dimensions of the various elements that collectively define the socket, the particular shape of the socket is also not intended to be limiting. As shown in FIGS. 2 and 3, the preferred socket has a cylindrical shape with a widened socket opening and sidewalls that have a tapered section proximate to the narrowed base. Alternatively, the sidewalls of the socket could have a uniform taper from their superior end surrounding the socket opening to their inferior ends connected to the base. Furthermore, the socket could take any number of shapes without departing from the innovative aspects discussed herein, including but not limited to a square or rectangular shape with vertical sidewalls.

To prevent water entrapment within the socket, drain ports 36 are provided with separate portions within the sidewall and the base. As particularly shown in FIGS. 4A, 4B and 4C, drain ports are provided on the medial and lateral sides of the socket. So that water has more ways to escape that through single holes in the bottom base portion of the socket, the drain ports are enlarged and have a first portion 36a within the sidewalls as well as a second portion 36b within the base proximate to location where the sidewalls connect to the base. Accordingly, not only can water can drain out of the socket through the second portions of the drain ports within the base when the device is oriented vertically, such as when it is in use, but water can also drain out of the first portions of the drain ports that are situated within the sidewalls, such as when the device is laying on its side and not in use. Drainage is further assured by the openings 50 in the liner that align with the drain ports, best shown in FIGS. 4B and 4C, so as not to obstruct the flow of water out of the socket. Furthermore, the drain holes also allow a wearer to more easily swap out liner pads by providing an additional access point into the interior of the socket from the side or bottom in addition to the socket opening opposite from the base.

As noted above, the socket is formed from a rigid unitary material and therefore provides the structural support to the device and wearer but does not form to the limb of the wearer or dependently secure to the limb of the wearer. To secure the residual limb within the socket and provide a comfortable fit, a liner is removably positioned within the interior of the socket. The liner has an outer side that releasably attaches one or more mounting points on the socket sidewalls and socket base. The liner has a thickness between the inner side and the outer side such that when the residual limb is inserted into the socket opening and contacts the inner side of the liner, the liner slightly deforms and compresses into an engaged position 48 which holds the residual limb with a friction fit.

As referenced above, the liner 14 is secured to one or more mounting points 30 within the interior of the socket. To allow for customization by the wearer, it is an aspect of the device to include mounting points on each of the sidewall sections and the base of the socket such that the wearer may optionally insert a liner that attaches to any number of the mounting points, but not necessarily all. Furthermore, although the preferred embodiment uses a friction fit between recesses and apertures within the socket and protrusions in the liner to secure the liner within the socket, any type of fastening means could be provided at the various mounting points without departing from the inventive aspect of the prosthetic described herein. For example, the mounting points could include a hook and loop fastener, a releasable snap-fit joint, a snap, a button or any other fastener that can be quickly and easily connected and released to releasably attach the liner into the socket.

In the preferred embodiment, the liner sections include protrusions 54 on the outer side that are received within recesses 30a or apertures 30b within the sidewall and base of the socket. As more particularly illustrated in the exploded view of FIG. 2B, the mounting point on the medial section and the lateral section consist of apertures that extend from the drain ports discussed above. Conversely, the mounting points on each of the anterior section, the posterior section and the base consist of recesses within the interior of the socket. To secure the liner at these various mounting points, protrusions are inserted into the respective apertures and recesses such and held in place by a friction fit. Subsequently, the wearer can quickly pull the liner sections free from the various mounting points for cleaning or further customization of the device fitment.

As noted herein, it is an aspect of the invention to include a modular liner that allows a wearer to select a particular liner having a desired thickness ($T_L$) between outer 46a and inner 46b sides to fit the wearers needs in addition to having a modular construction to allow a wearer to select particular portions of the socket that have a liner. Accordingly, the liner is modular kit collectively made up of a selection of interchangeable pads 38 that are inserted into the socket in a kit assembly and form a space 40 that holds the residual limb. As more particularly illustrated in the exploded view of FIG. 2B, a complete liner kit 52a includes a pad corresponding with each interior portion of the socket, namely an anterior pad 38a, a posterior pad 38b, a medial pad 38c, a lateral pad 38d and an inferior pad 38e. In a full kit assembly, a pad is releasably attached at each of the mounting points but a wearer may elect to only have a partial kit assembly 52b by removing at least one of the pads. Furthermore, the inventive prosthetic described herein allows a wearer to mix and match pad kits that have differing thicknesses such that the wearer is not beholden to a single kit for use within a socket.

In operation, the wearer can select which pads suit them best from various kits and attach the pads to the various mounting points within the socket. For example, a wearer may elect to have a thicker anterior pad from one kit and a thinner posterior pad from another kit. In another example, the wearer may elect to remove the lateral and medial pads all together from an otherwise fill kit assembly if they determine this provides a better or more secure fit for their use. Further still, a wearer may select a thinner kit of pads that creates a less secure friction fit when showering with the device to allow for easier access to washing the distal end of the wearer's leg. Conversely, another wearer may want thicker pads that provide a more secure friction fit while washing because the present invention allows the wearer to easily remove their leg from the socket and use the handle to help balance while washing the leg's distal end.

The ability to interchange specific pads from various kits also allows the use of a single design for various types of amputees. As referenced herein, the device can be worn by both above and below the knee amputees who need only swap out the removable liners based on their specific need. Although the geometry of the superior end of the socket discussed above provides a more ergonomic fit for below the knee amputees, this construction does not preclude the use of the device for above the knee amputees.

Regardless of the particular pad and configuration the wearer chooses, it will be appreciated that each kit includes corresponding pads for each section of the socket interior such that the anterior pad releasably connects to the mounting point on the anterior section, the posterior pad releasably connects to the mounting point on the posterior section, the inferior pad releasably connects to the mounting point on the base, the medial pad releasably connects to the mounting point on the medial section, and the lateral pad releasably connects to the mounting point on the lateral section.

In addition to custom pad placement and thickness outlined above, the variations in the liner and pad kits allow a wearer to not only customize the fit at the outset but also grow with the socket and continue to modify the fit. For example, a teen or young adult who is not done growing can use the socket of the prosthetic described herein as they continue to grow by simply interchanging the liner pads as needed. The interchangeable pad design therefore allows wearer customization while also providing a uniform build size for manufacturers, thereby reducing manufacturing costs. Finally, removable liners allow for easier cleaning of the pads themselves and other parts of the device.

As noted above, the preferred pads that make up the liner are formed from a RIM soft durometer foam that may foldable or bendable to fit within the socket. The pads may be wholly separate from one another as shown FIG. 2B are may be partially or completely connected as illustrated in the alternative pad designs of FIG. 6. FIGS. 6A and 6B show particular alternative embodiments with each of the anterior, posterior, lateral and medial pad segments connected to the inferior edge. Other pad variations may have some pad segments that are connected together while others remain separate. For example, FIG. 6C shows a liner with the anterior pad and the posterior pad connected to the interior pad while the medial pad and lateral pad remain separate. Regardless of the pad configuration within a liner, it will be understood that the various pad segments releasably attach to the respective mounting points on the interior of the socket as explained above.

When one or more pad sections are connected together, it will be appreciated that the inferior pad has a perimeter edge 56 with each of the other pads having a fixed end 58 connected to the perimeter of the inferior edge. To promote easier folding of the pad segments that are connected together, the preferred embodiment includes a living hinge 60 with a reduced thickness ($RT_L$) between the perimeter edge of the inferior pad and the fixed end of each pad connected thereto. This reduced thickness promotes easier folding of the liner and thereby easier installation.

To provide additional support and stability, the prosthetic described herein also includes a handle 16 protruding from the superior end of one of the socket sidewalls as particularly shown in FIG. 5. The handle allows the wearer to maintain engagement in the device and provides another point of control for the device to assure safety and security. Preferably, the handle extends from the anterior section on the front side of the device within an anterior plane 90 but it will appreciated that the handle could be positioned on the superior end of another wall without departing the inventive features described. The handle includes a post 62 with a post length ($L_{HP}$) spacing a post inferior end 62a connected to the sidewall of the socket and a post superior end 62b supporting an arcuate grip 64.

Figure 5D:
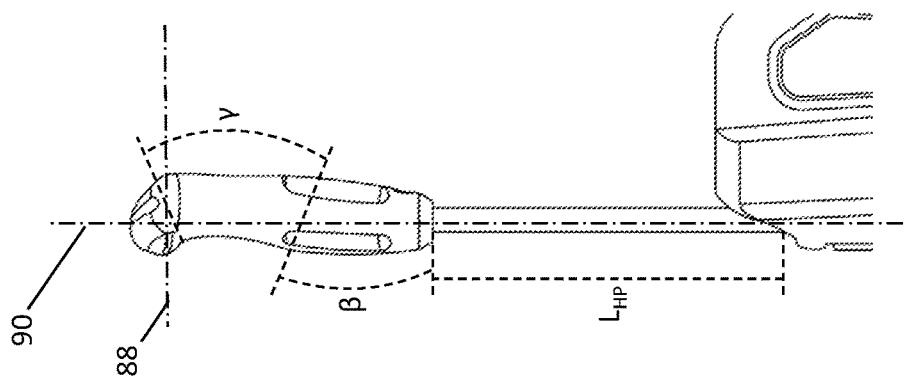
FIGS. 5A, 5B, 5C and 5D respectively show a rear three-quarter perspective view, a front three-quarter perspective view, a front view and a side view of the handle according to the preferred embodiment of the invention described herein.
Figure 5C:
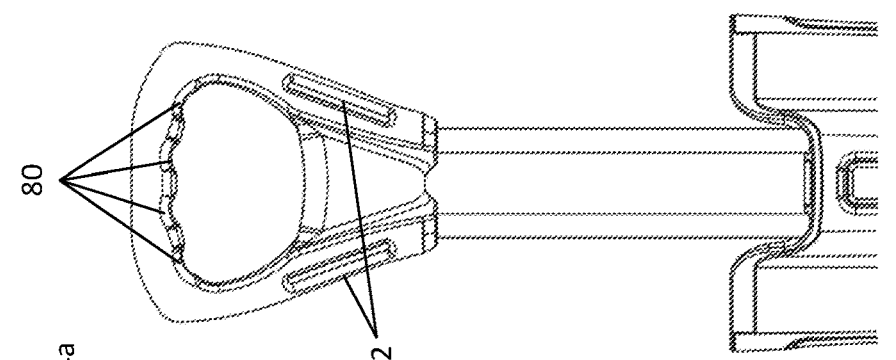
Figure 5B:
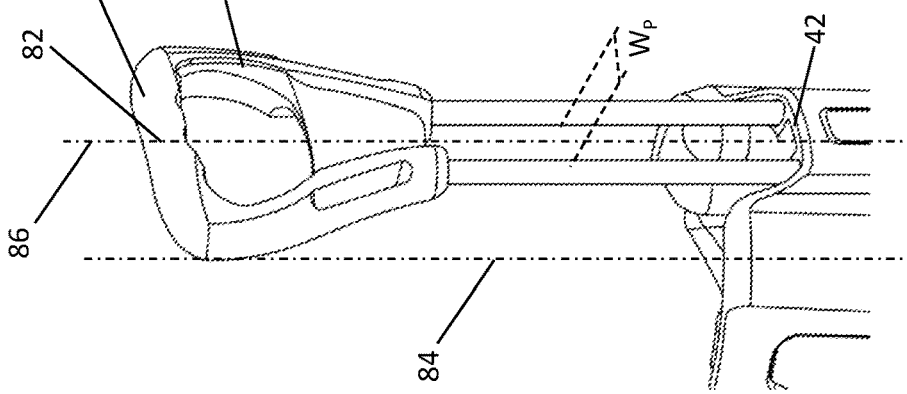

In the preferred embodiment the arcuate grip has a center point 82 that is situated along an anterior vertical axis 86 that is radially spaced from a central vertical axis 84 that extends through the respective center point of each of the socket opening 94a, the base 94b and the pylon 94c. Although alternative embodiments may have handles with a curved post, the preferred handle according to the invention described herein not only has a straight post that is situated within an anterior plane in which the anterior vertical axis lies but also has a pair of posts spaced by a width ($W_P$) within the anterior plane on opposite sides of the anterior vertical axis. Furthermore, as shown in FIGS. 5B and 5C, the inferior ends of the posts attach to the superior end of the sidewall within the inferiorly recessed segment.

The dual post design provides a more secure connection between the socket and the arcuate grip and prevents rotation of the prosthetic because each post can contact the leg of the wearer at two locations. Furthermore, offsetting the posts from the anterior vertical axis and providing a space therebetween provides clearance for the kneecap 110 of wearer during flexion. If a single post is used, the post may tend to interfere with knee flexion.

The post may be telescopic in nature to accommodate wearers of varying heights or similarly have a height adjustment mechanism. It will be appreciated that a tubular post, similar to the pylon discussed below, could be used to allow for the change in the handle's height above the socket. The post could also be a pair of rods that have notches along their length which engage a releasable catch or ratchet mechanism within the socket on which the post is attached. The post may also be easily removable to allow for condensed storage or travel requirements.

Figure 5A:
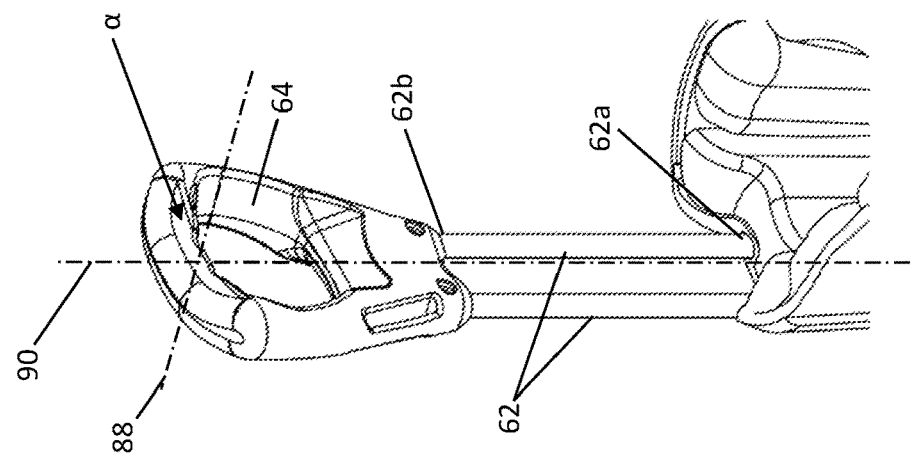
Figure 8:
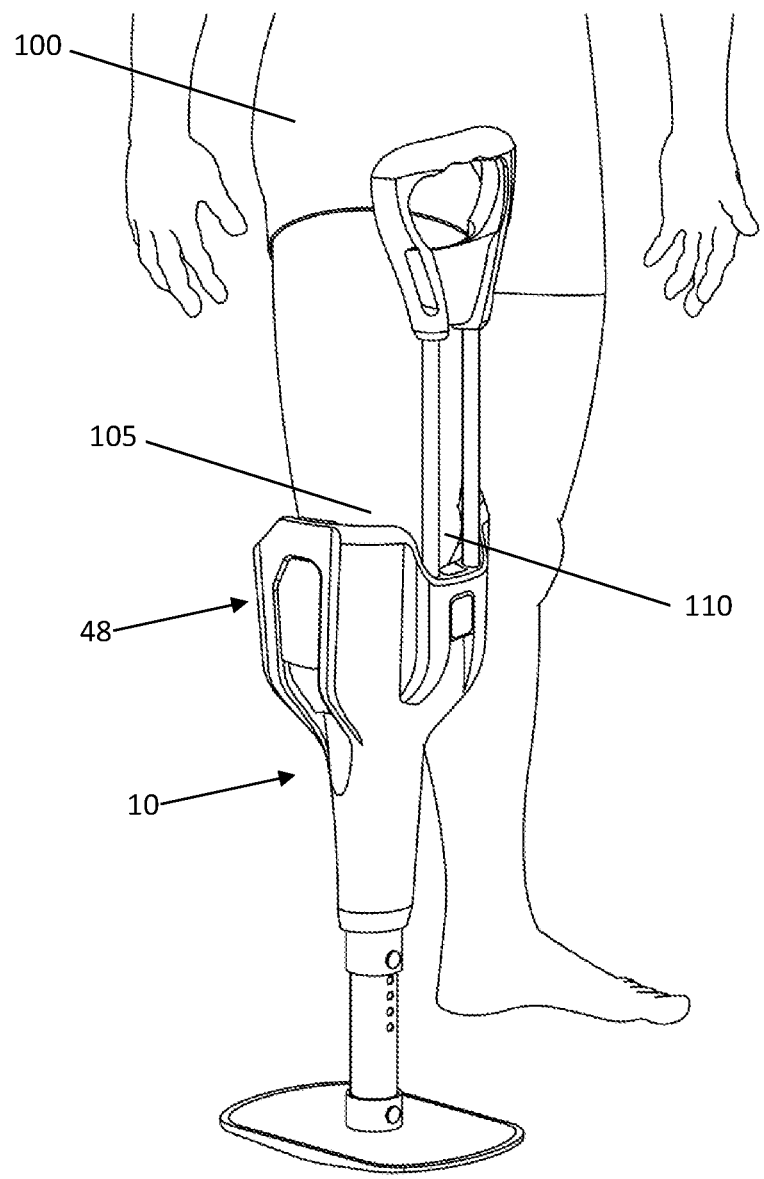
FIG. 8 shows a perspective view of the prosthetic device according to the invention described herein being worn by a person with a residual limb.

Regardless of whether the handle includes a single or dual post constriction, the arcuate handle has at least one angle of curvature designed to contour to the leg of the wearer. As shown in FIGS. 3A and 5A, a first angle of curvature ($\alpha$) is provided in the hand section 64a that is angled about the anterior vertical axis within a transverse plane 88. This angle thereby allows the hand section of the handle to at least partially wrap around the leg the wearer and provide additional stability and control. By comparison, a linear handle, such as those in the prior art, does not contour to the shape of the leg and only provides a single contact point, thus rendering the handle less effective when not being grasped. The preferred arcuate grip also includes one or more angles of curvature ($\beta$ and $\gamma$) within the body 64b of the grip that is situated beneath the hand section. These secondary curves increase the ergonomic benefit of the handle and reduce the likelihood of interference with the thigh of the wearer which may occur with straight grip sections. The curvature of the handle thereby provides a more ergonomic fit and use for the wearer and the ergonomics may be further improved by providing indexed sections 80 in the hand section of the grip. The indexed sections align with the fingers of the wearers hand so that the grip can be grasped more firmly and comfortably.

In another alternative embodiment, the handle may have a strap 66 with an end 68 that can be fastened into a secured arrangement around the leg of a wearer while the residual limb is engaged with the socket or released in an unsecured arrangement. When secured, the strap applies a radial force onto the leg of the residual limb at a location 96 spaced a distance (D) above the socket. Accordingly, the prosthetic with a strap not only has a friction fit within the socket but also has a secondary fit with the strap that holds the limb in a secured position. The strap allows the wearer to maintain use of both hands, if desired, while using the device. However, it is an aspect of the invention to only require the friction fit provided by the pads of the liner to hold the device in place and the adjustment strap is therefore an optional feature for added security.

According to the preferred embodiment of the device with a strap as shown in FIG. 3, the body of the handle includes a pair of slots 72 through which the strap is inserted. The straps subsequently fasten with a fastener 74 on their distal ends, posterior to the body and residual limb that is held within the socket. As with the pads that secure to the mounting points on the sidewall sections of the socket discussed above, the particular type of fastener is not intended to be limiting and may include but is not limited to a hook and loop fastener, a releasable snap-fit joint, a snap, a button or any other fastener that can be quickly and easily connected and released.

To support the socket and residual limb held therein, a pylon 18 extends from the underside of the socket to a footplate that engages the ground. The pylon includes a proximal end 18a attached to the exterior of the socket and spaced by a pylon length ($L_P$) from the distal end 18b connected to the footplate. As referenced above and shown in FIG. 3E, the preferred construction of the socket includes a bore within a longitudinal protrusion that receives the proximal end of the pylon although alterative designs may not have a longitudinal protrusion on the exterior of the socket.

Regardless of the socket design, it is preferred that the pylon has a variable length so the height of the prosthetic can be adjusted by the wearer. Thus, the preferred pylon includes a plurality of telescoping sections 76 and a coupler 78 between the telescoping sections such that the proximal end of the pylon is situated within a first section 76a and the distal end of the pylon is situated within a second section 76b. In operation, adjusting the telescoping sections relative to one another can move the pylon between an extended length and a recessed length. In combination, the adjustable pylon and adjustable handle therefore allows a single device to accommodate wearer's who have amputations at differing locations. For example, a below the knee amputee will need a shorter pylon and longer handle whereas an amputee who has an above the knee amputation may need a longer pylon and shorter handle.

The orientation of the telescoping sections are further configured to prevent water from entering through the top end of the upper sections. Accordingly, the lower sections nest within the upper sections and the bore of the longitudinal protrusion in the socket envelops the proximal end of the pylon in the preferred embodiment. If any water does seep into the telescoping sections, an aperture 92 is provided in the foot to allow drainage.

Although the particular coupler used to hold the various telescoping sections in their respective positions to reach a desired length is not intended to be limiting, the preferred coupler shown includes a series of apertures 108 and a corresponding pin 112 within the various sections. In operation, the respective apertures in the different sections align and the wearer inserts one or more pins to the lock the sections in place at the selected length. Alternatively, a spring-loaded nub at the end of each section may be provided in place of the pin. In operation, the nub is biased outwardly towards the series of apertures and extends through the apertures as the sections are moved relative to one another. This design requires the wearer to depress the nub until the desired length is reached but eliminates the need for a separate pin. Another type of telescoping pylon might have a clamp coupler assembly at the interface between various sections and it will be understood that any type of telescoping pylon could be used to provide for the adjustable height of the device.

The footplate 20 attached to the distal end of the pylon includes a foot pad 70 with bottom surface made from a gripping material 98a, such as rubber, as well as a unique geometric pattern 98b which assure omni directional stability on the highly irregular and slippery surfaces located in showers. The foot pad may also contain a large radius to facilitate a more natural walking motion. The footplate of the device may also contain features such as a full-flat bottom to allow the device to be freestanding. Depending on the size and needs of the wearer, the device may also contain options for various size foot pads. These pads may differ in width, length, lower surface curvature and types of surface features to promote grip or stability for a variety of surfaces.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, antimicrobial treatments or additives may be used to further reduce infection risk of the wearer. Furthermore, the device has been specifically designed to be lightweight (<6 lbs) but lighter or heavier designs may be made without departing from the inventive features described herein. Thus, the breadth and scope of the present invention should not be limited by any of the above-described exemplary embodiments, but should be defined only in accordance with the following claims appended hereto and their equivalents.

What is claimed is:

1. A prosthetic leg for a residual limb, comprising: a socket comprising a socket opening, a base, a sidewall, an interior, an exterior and a mounting point on the interior of the sidewall, wherein sidewall extends a sidewall length from a sidewall inferior end to a sidewall superior end, wherein the sidewall inferior end connects around a perimeter of the base, and wherein the sidewall superior end surrounds the socket opening; a liner removably situated within the interior of the socket, wherein the liner comprises an outer side and an inner side spaced by a liner thickness, wherein the outer side releasably attaches to the mounting point, wherein the residual limb is inserted into the socket opening and abuts the inner side of the liner in an engaged position, and wherein the liner holds the residual limb in the engaged position with a friction fit; a handle comprising a post and an arcuate grip, wherein the post comprises a post inferior end and a post superior end spaced by a post length, wherein the post inferior end is connected to the superior end of the sidewall, and wherein the arcuate grip is connected to the post superior end opposite from the post inferior end, and wherein the handle further comprises a second post parallel to the post and a strap having at least one end which moves between a secured arrangement and an unsecured arrangement while the residual limb is in the engaged position;

a pylon comprising a proximal end and a distal end spaced by a length, and wherein the proximal end is connected to the socket on the exterior of the base, wherein the socket opening, the base, the pylon and the arcuate grip each further comprise a center point, wherein the center point of the socket opening, the base, and the pylon are situated along a central vertical axis, wherein the superior end of the sidewall is radially spaced around the central vertical axis, wherein the center point of the arcuate grip is situated along an anterior vertical axis radially spaced from the central vertical axis, wherein the post and the other post are spaced by a width within an anterior plane on opposite sides of the anterior vertical axis, wherein the body further comprises a pair of slots on opposite sides of the anterior vertical axis, and wherein the strap extends through the slots and comprises a fastener posterior to the body;

and a footplate connected to the distal end of the pylon.

2. The prosthetic of claim 1, wherein the socket further comprises a drain port, wherein the drain port comprises a first portion situated within the sidewall and a second portion situated within the base, and wherein the liner further comprises an opening aligned with at least a portion of the drain port.

3. The prosthetic of claim 1, wherein the sidewall further comprise an anterior section, a posterior section, a medial section and a lateral section, wherein the mounting point further comprises a respective mounting point in each of the anterior section, the posterior section, the medial section, the lateral section and the base, wherein the liner further comprises a kit of modular pads comprising an anterior pad, a posterior pad, a medial pad, a lateral pad, and an inferior pad, and wherein at least one of the anterior pad, the posterior pad, the medial pad, the lateral pad, and the inferior pad are releasably connected to the corresponding mounting point on the anterior section, the posterior section, the medial section, the lateral section and the base.

4. The prosthetic of claim 3, wherein each of the anterior pad, the posterior pad, the medial pad, the lateral pad, and the inferior pad are releasably connected to the respective mounting point on the anterior section, the posterior section, the medial section, the lateral section and the base in a full kit assembly, and wherein at least one of the anterior pad, the posterior pad, the medial pad, the lateral pad, and the inferior pad are removed from the respective mounting point on the anterior section, the posterior section, the medial section, the lateral section and the base in a partial kit assembly.

5. The prosthetic of claim 3, wherein the respective mounting point on each of the medial section and the lateral section comprise an aperture in the sidewall, wherein the mounting point on each of the anterior section, the posterior section and the base comprise a recess, wherein the outer side of each of the anterior pad, the posterior pad, the medial pad, the lateral pad and the inferior pad further comprise a protrusion, wherein the respective protrusions on the anterior pad, the posterior pad and the inferior pad are received in the respective recesses in the anterior section, the posterior section and the base, and wherein the respective protrusions on the medial pad and the lateral pad are received in the respective apertures in the medial section and the lateral section.

6. The prosthetic of claim 3, wherein the inferior pad further comprises a perimeter edge, and wherein at least one of the anterior pad, the posterior pad, the medial pad and the lateral pad further comprise a fixed end connected to the perimeter edge of the inferior pad.

7. The prosthetic of claim 6, further comprising a living hinge between the perimeter edge of the inferior pad and the fixed end of at least one of the anterior pad, the posterior pad, the medial pad and the lateral pad connected thereto, and wherein the liner thickness further comprises a reduced pad thickness at the living hinge.

8. The prosthetic of claim 3, wherein the anterior section is anterior of the central vertical axis, wherein the posterior section is posterior of the central vertical axis, wherein the medial section is medial of the central vertical axis, and wherein the lateral section is lateral of the central vertical axis.

9. The prosthetic of claim 1, wherein the anterior vertical axis is anterior to the central vertical axis.

10. The prosthetic of claim 1, wherein the arcuate grip further comprises a hand section and a body, wherein the hand section comprises a first angle of curvature within a transverse plane, wherein an anterior section of the sidewall further comprises an inferiorly recessed segment relative to the superior end of at least one of a lateral section and a medial section of the socket, and wherein a posterior section of the sidewall is sloped inferiorly downward from of at least one of a lateral section and a medial section of the socket.

11. The prosthetic of claim 1, wherein the pylon further comprises a plurality of telescoping sections and a coupler between the telescoping sections, wherein the post of the handle further comprises an adjustable height, wherein the arcuate grip of the handle further comprises a plurality of indexed surfaces, and wherein the footplate further comprises a bottom surface having a gripping material.

12. A prosthetic leg for a residual limb, comprising:
a socket comprising a socket opening, a base, a sidewall, an interior and an exterior, wherein the sidewall comprises an anterior section, a posterior section, a medial section and a lateral section respectively extending a sidewall length from a sidewall inferior end to a sidewall superior end, wherein the inferior ends of the sidewall sections are connected around a perimeter of the base, wherein the superior ends of the sidewall sections surround the socket opening, and wherein the anterior section, the posterior section, the medial section, the lateral section and the base each further comprising a respective mounting point;
a liner removably situated within the interior of the socket, wherein the liner comprises a kit of modular pads comprising an anterior pad, a posterior pad, a medial pad, a lateral pad, and an inferior pad, wherein each of the anterior pad, the posterior pad, the medial pad, the lateral pad, and the inferior pad comprise an outer side spaced from an inner side by a pad thickness, wherein at least one of the anterior pad, the posterior pad, the medial pad, the lateral pad, and the inferior pad are releasably connected to the respective mounting point on the anterior section, the posterior section, the medial section, the lateral section and the base in a kit assembly, wherein the residual limb is inserted into the socket opening and abuts the inner side of at least one of the anterior pad, the posterior pad, the medial pad, the lateral pad, and the inferior pad in an engaged position, wherein the liner holds the residual limb in the engaged position with a friction fit, wherein the respective mounting point on each of the medial section and the lateral section comprise an aperture in the sidewall, wherein the mounting point on each of the anterior section, the posterior section and the base comprise a recess, wherein the outer side of each of the anterior pad, the posterior pad, the medical pad, the lateral pad and the interior pad further comprise a protrusion, wherein the respective protrusions on the anterior pad, the posterior pad and the inferior pad are received in the respective recesses in the anterior section, the posterior section and the base, and wherein the respective protrusions on the medial pad and the lateral pad are received in the respective in the respective apertures in the medial section and the lateral section;

a handle comprising a post and an arcuate grip, wherein the post comprises a post inferior end and a post superior end spaced by a post length along an anterior vertical axis, wherein the post inferior end is connected to the superior end of the anterior section of the sidewall, wherein the arcuate grip is connected to the post superior end opposite from the post inferior end, wherein the arcuate grip further comprises a hand section and a body, wherein the hand section comprises a first angle of curvature within a transverse plane, and wherein the anterior vertical axis is radially spaced from a center vertical axis which intersects a center point of the socket opening and the base;

a pylon comprising a proximal end and a distal end spaced by a length, and wherein the proximal end is connected to the socket on the exterior of the socket; and a footplate connected to the distal end of the pylon.

13. The prosthetic of claim 12, wherein the anterior vertical axis is anterior to the central vertical axis.

14. The prosthetic of claim 12, wherein the inferior pad further comprises a perimeter edge, and wherein at least one of the anterior pad, the posterior pad, the medial pad and the lateral pad further comprise a fixed end connected to the perimeter edge of the inferior pad.

15. The prosthetic of claim 12, wherein the socket further comprises a drain port, wherein drain port comprises a first portion situated within at least one the anterior section, the posterior section, the medial section and the lateral section of the sidewall and a second portion situated within the base, and wherein the liner further comprises an opening aligned with a least a portion of the drain port.

16. The prosthetic of claim 12, wherein the anterior section of the sidewall further comprises an inferiorly recessed segment relative to the superior end of at least one of the lateral section and the medial section of the socket, wherein the posterior section of the sidewall is sloped inferiorly downward from of at least one of a lateral section and a medial section of the socket, and wherein the post inferior end of the handle is connected to the inferiorly recessed segment within the superior end of the anterior section.

17. A prosthetic leg for a residual limb, comprising:

a socket comprising a socket opening, a base, a sidewall, an interior and an exterior, wherein the sidewall comprises an anterior section, a posterior section, a medial section and a lateral section respectively extending a sidewall length from a sidewall inferior end to a sidewall superior end, wherein the inferior ends of the sidewall sections are connected around a perimeter of the base, wherein the superior ends of the sidewall sections surround the socket opening, wherein the anterior section of the sidewall further comprises an inferiorly recessed segment relative to the superior end of at least one of the lateral section and the medial section of the socket, wherein the posterior section of the sidewall is sloped inferiorly downward from of at least one of the lateral section and the medial section of the socket, and wherein the anterior section, the posterior section, the medial section, the lateral section and the base each further comprising a respective mounting point;

a liner removably situated within the interior of the socket, wherein the liner comprises a kit of modular pads comprising an anterior pad, a posterior pad, a medial pad, a lateral pad, and an inferior pad, wherein each of the anterior pad, the posterior pad, the medial pad, the lateral pad, and the inferior pad comprise an outer side spaced from an inner side by a pad thickness, wherein at least one of the anterior pad, the posterior pad, the medial pad, the lateral pad, and the inferior pad are releasably connected to the respective mounting point on the anterior section, the posterior section, the medial section, the lateral section and the base in a kit assembly, wherein the residual limb is inserted into the socket opening and abuts the inner side of at least one of the anterior pad, the posterior pad, the medial pad, the lateral pad, and the inferior pad in an engaged position, and wherein the liner holds the residual limb in the engaged position with a friction fit;

a handle comprising a pair of posts and an arcuate grip, wherein each of the posts comprise a post inferior end and a post superior end spaced by a post length along an anterior vertical axis, wherein the post inferior ends are connected to the inferiorly recessed segment within the superior end of the anterior section, wherein the posts are spaced by a width within an anterior plane on opposite sides of the anterior vertical axis, wherein the arcuate grip is connected to the post superior ends opposite from the post inferior ends, wherein the arcuate grip further comprises a hand section and a body, wherein the hand section comprises a first angle of curvature within a transverse plane, and wherein the anterior vertical axis is radially spaced from a center vertical axis which intersects a center point of the socket opening and the base;

a pylon comprising a proximal end and a distal end spaced by a length, and wherein the proximal end is connected to the socket on the exterior of the socket; and a footplate connected to the distal end of the pylon.

18. The prosthetic of claim 17, wherein the respective mounting point on each of the medial section and the lateral section comprise an aperture in the sidewall, wherein the mounting point on each of the anterior section, the posterior section and the base comprise a recess, wherein the outer side of each of the anterior pad, the posterior pad, the medial pad, the lateral pad and the inferior pad further comprise a protrusion, wherein the respective protrusions on the anterior pad, the posterior pad and the inferior pad are received in the respective recesses in the anterior section, the posterior section and the base, wherein the respective protrusions on the medial pad and the lateral pad are received in the respective apertures in the medial section and the lateral section, wherein the inferior pad further comprises a perimeter edge, and wherein at least one of the anterior pad, the posterior pad, the medial pad and the lateral pad further comprise a fixed end connected to the perimeter edge of the inferior pad.

19. The prosthetic of claim 17, wherein the socket further comprises a drain port, wherein drain port comprises a first portion situated within at least one the anterior section, the posterior section, the medial section and the lateral section of the sidewall and a second portion situated within the base, and wherein the liner further comprises an opening aligned with a least a portion of the drain port.

20. The prosthetic of claim 17, wherein the handle further comprises a strap having at least one end which moves between a secured arrangement and an unsecured arrangement while the residual limb is in the engaged position, wherein the body further comprises a pair of slots on opposite sides of the anterior vertical axis, and wherein the strap extends through the slots and comprises a fastener posterior to the body.

* * * * *